United States Patent
Reiber et al.

(10) Patent No.: US 10,736,978 B2
(45) Date of Patent: Aug. 11, 2020

(54) PORTABLE DISINFECTION DEVICE

(71) Applicants: Braden A. Reiber, Parker, CO (US); Phillip D. Wright, Fort Collins, CO (US)

(72) Inventors: Braden A. Reiber, Parker, CO (US); Phillip D. Wright, Fort Collins, CO (US)

( * ) Notice: Subject to any disclaimer, the term of this patent is extended or adjusted under 35 U.S.C. 154(b) by 320 days.

(21) Appl. No.: 15/683,461

(22) Filed: Aug. 22, 2017

(65) Prior Publication Data

US 2018/0055960 A1    Mar. 1, 2018

Related U.S. Application Data

(60) Provisional application No. 62/494,863, filed on Aug. 23, 2016.

(51) Int. Cl.
*A61L 2/10*     (2006.01)
*C02F 1/32*     (2006.01)

(52) U.S. Cl.
CPC ............... *A61L 2/10* (2013.01); *C02F 1/325* (2013.01); *A61L 2202/11* (2013.01); *A61L 2202/14* (2013.01); *A61L 2202/16* (2013.01); *C02F 2201/009* (2013.01); *C02F 2201/3222* (2013.01); *C02F 2201/3227* (2013.01); *C02F 2209/005* (2013.01); *C02F 2209/008* (2013.01); *C02F 2303/04* (2013.01); *C02F 2307/02* (2013.01); *C02F 2307/04* (2013.01)

(58) Field of Classification Search
CPC ....................................................... A61L 2/10
See application file for complete search history.

(56) References Cited

U.S. PATENT DOCUMENTS

| | | | |
|---|---|---|---|
| 4,389,311 A | * | 6/1983 | La Freniere ............ C02F 1/002 141/98 |
| 4,971,687 A | * | 11/1990 | Anderson ............... C02F 1/283 210/232 |
| 5,671,840 A | * | 9/1997 | Glicksman ............... H01H 9/04 200/302.2 |
| 5,900,212 A | | 5/1999 | Maiden et al. |
| 6,110,424 A | | 8/2000 | Maiden et al. |
| 6,579,495 B1 | | 6/2003 | Maiden |

(Continued)

FOREIGN PATENT DOCUMENTS

| | | |
|---|---|---|
| CN | 201420274934 U | 9/2014 |
| JP | 2012262959 A | 6/2014 |
| KR | 2013 0143281 A | 12/2013 |

OTHER PUBLICATIONS

Rayvio UV Disenfecting Water Bottle, Radius (date is unknown).

(Continued)

*Primary Examiner* — Donald R Spamer
(74) *Attorney, Agent, or Firm* — Caroline Nash

(57) ABSTRACT

A small, hands free, portable, rechargeable, waterproof, UV-C light emitting disinfection device. The disinfection device has a durable outer housing that holds an array of externally facing Ultraviolet C spectrum (UV-C) Light Emitting (LEDs) that emit light within the germicidal range of the Ultraviolet C spectrum or between the wavelength($\lambda$) range of 200 nm to 280 nm. The disinfection unit can be deployed in a water bottle, backpack bladder, water jug, or any suitable container to disinfect water or other liquids.

44 Claims, 13 Drawing Sheets

(56) References Cited

U.S. PATENT DOCUMENTS

| | | | |
|---|---|---|---|
| 6,870,089 B1* | 3/2005 | Gray | H02S 10/40 |
| | | | 136/251 |
| 7,550,089 B2 | 6/2009 | Kuhlmann | |
| 8,362,432 B2 | 1/2013 | Maiden | |
| D707,124 S | 6/2014 | Blain et al. | |
| 2002/0046569 A1 | 4/2002 | Faqih | |
| 2006/0138443 A1* | 6/2006 | Fan | H01L 33/56 |
| | | | 257/100 |
| 2006/0196900 A1* | 9/2006 | Sasick | A45F 5/00 |
| | | | 224/183 |
| 2006/0207267 A1* | 9/2006 | Erdman | F24F 3/166 |
| | | | 62/78 |
| 2008/0035581 A1* | 2/2008 | Kuhlmann | C02F 1/325 |
| | | | 210/748.11 |
| 2008/0095661 A1* | 4/2008 | Kohler | A61L 9/20 |
| | | | 422/20 |
| 2008/0118411 A1* | 5/2008 | D'Arinzo | A61L 2/202 |
| | | | 422/186.09 |
| 2008/0260601 A1* | 10/2008 | Lyon | A61L 2/10 |
| | | | 422/186.3 |
| 2009/0139927 A1 | 6/2009 | Kania | |
| 2010/0102252 A1* | 4/2010 | Harmon | A61L 2/10 |
| | | | 250/492.1 |
| 2011/0226966 A1* | 9/2011 | Takahashi | A01K 63/04 |
| | | | 250/492.1 |
| 2012/0294787 A1 | 11/2012 | Meszaros | |
| 2013/0146783 A1* | 6/2013 | Boodaghians | C02F 1/325 |
| | | | 250/435 |
| 2014/0319374 A1* | 10/2014 | Chandler | A61L 2/10 |
| | | | 250/455.11 |
| 2015/0166368 A1 | 6/2015 | Braunberger | |
| 2015/0250907 A1* | 9/2015 | Bilenko | A61L 2/10 |
| | | | 250/454.11 |
| 2016/0354503 A1* | 12/2016 | Hutchens | A61L 2/10 |

OTHER PUBLICATIONS

Ellie Kills 99.9% of Germs in Just 60 Seconds (date unknown).
Hello Backers, We are Team Cleanty Sep. 13, 2017.
Orb the Worlds First Germ Killing Blue/UV Light Ball (Mar. 2017).

\* cited by examiner

PORTABLE DISINFECTION DEVICE

This application claims priority of U.S. Ser. No. 62/494,863 filed Aug. 23, 2016.

BACKGROUND OF THE INVENTION

1 Field of the Invention

The invention relates to the field of disinfection devices using Ultra Violet (UV) light. More specifically, the invention relates to a small, hands free, portable, rechargeable, waterproof, UV-C light emitting disinfection device with an optional auxiliary, solar powered induction recharging system.

2 Brief Description of Related Art

There are various methods for sterilizing refilled water in a personal water container such as a "Nalgene®" bottle or "Hydro Flask®" container. These methods include portable filtration systems such as "LifeStraw®" or "Platypus GravityWorks®" filters, chlorine, hydrogen peroxide or iodine tablets such as "Portable-Aqua®" and, finally, personal UV-C sterilization units such as "Steripen®" and "Camelbak® All Clear".

Filtration systems, while mostly effective, do not completely disinfect, are generally cumbersome to carry, complicated to use, time consuming, and expensive. These filtration systems typically consist of multiple large parts such as a bladder or pair of bladders with feed tubes and a microbial filter to filter out the water. However, the filter itself is only capable of filtering out larger microorganisms and particles. Smaller microorganisms, like viruses and bacteria, can still pass through the filter and find their way into the drinking water. In addition, set up can take several minutes and more time required to filter the water. Another downfall of these devices is that the filter has a limited life span. Eventually, the filter becomes clogged with all the past microbes and debris that were filtered out of the water and the filter must be replaced adding extra cost to an already expensive device.

Chemically treating water, while extremely effective, can alter the taste of the water while also adding unwanted chemicals. The manufacturers of these chemical methods warn against continuous use, for health reasons, as ingesting too much of the treatment can be harmful over time. And lastly, these chemical treatments are relatively expensive as a long-term solution, as they are consumed and must be replaced after each use.

UV-C light is the most effective, easy to use and economical method on the market. However, the currently available products are both bulky in their design and cumbersome to handle, requiring the user to stop for the length of time that it takes to treat all the water needing disinfection. When gear weight is an issue for longer periods of travel or hiking, these devices can add substantial and un-wanted weight to someone's backpack, bag or luggage.

The most widely used UV-C radiation emitters in the industry today are mercury lamps encapsulated in a quartz sleeve. These devices adequately produce ultraviolet light within the desired germicidal range, but carry some inherent drawbacks. The quartz sleeve is fragile and better suited for applications where the emitter is not exposed to external conditions. The lamp contains toxic mercury. In addition, the mercury lamps operate at relatively high voltage and may be less efficient than an LED (Light Emitting Diode). Thus, the characteristics of mercury lamps make it difficult to design portable personal devices that are rugged, compact and lightweight.

SUMMARY OF THE INVENTION

The invention is a small, hands free, portable, rechargeable, waterproof, UV-C light emitting disinfection device for water or liquid purification or disinfection. It may have an optional auxiliary, solar powered induction recharging system. The disinfection device has a durable outer housing that holds an array of externally facing Ultraviolet C spectrum (UV-C) Light Emitting Diodes (LEDs) that emit light within the germicidal range of the Ultraviolet C spectrum or between the wavelength($\lambda$) range of 200 nm to 280 nm. By utilizing UV-C LEDs mounted to a durable, lightweight outer housing, the disinfection device can be made smaller, and more efficient to use than the current UV-C methods.

The disinfection device can be deployed in a water bottle, backpack bladder, water jug, or any suitable container. The disinfection device of the invention may also be used out of the water for surface disinfection such as in a shoe, glove, or gym bag, or for any other circumstances needing disinfection, all without needing to stop and continually grasp the disinfection device by hand. The durable, waterproof housing of the invention serves to protect the internal components from damage from the normal wear and tear of use, as well as from exposure to liquids and other debris. The internal components of the invention are designed to be both weight and size conscious having either a single UV-C LED or an array of UV-C LEDs, flexible printed circuit board (PCBs) and/or rigid PCBs, rechargeable battery(s), battery charging and LED driver control circuitry, power and mode selection tactile switch, operational and mode indicator LEDs, waterproof micro USB and water sensing electrodes. Other embodiments may also include Bluetooth chips, induction coils, accelerometers, etc., to provide additional functionality.

The invention may have an optional an exterior case designed to provide protection for the disinfection device when not in use. A kit may include the disinfection device and one or more of the exterior case, USB cable and lanyard.

The exterior case can optionally provide a platform for solar cells to power an induction recharging system for recharging the battery inside the disinfection device. This method of recharging eliminates the need for large internal or external auxiliary batteries, or the need to be tethered to a wall outlet to recharge the device. In other embodiments, this protective charging case can use surface mounted, flexible solar panels, or photovoltaic coatings to collect solar radiation and convert it to electrical current providing reliable recharging on-the-go.

In the optional solar recharging configuration, electrical current is fed via the solar panels to a primary induction coil mounted in the case. This primary coil acts as a driving coil inducing a current in the secondary coil located in the disinfection unit. The secondary coil then feeds electrical energy to the battery, thus recharging the disinfection unit without any exposed leads or plugins. This configuration permits the disinfection device to be completely waterproof and entirely submersible in the water, thus, achieving an IP67 waterproof and debris rating. In other embodiments, the solar recharging system can supply power to the device through auxiliary power cords or any other means.

Other embodiments may include wireless connection devices such as a Bluetooth chip or a Wi-Fi card, accelerometers, motors, ac/dc plug-in for recharging from a wall source and any other component that may deliver additional functionality to the disinfection device. Other embodiments may also include other methods of recharging the battery that are not mentioned in the current embodiment of the design.

DETAILED DESCRIPTION

Today, outdoor enthusiasts, international travelers, adventure seekers, military special operators, etc., are constantly pushing the boundaries of the expedition, trip or mission, often finding themselves in places where natural and municipal water sources are of uncertain quality. In these circumstances, clean drinking water is vital and must be obtained in an efficient, safe, and effective manner.

Referring to the figures, the disinfection device A of the invention can be used in a multitude of applications that require disinfection, including personal water bottles and backpack bladders, water jugs or any suitable container. In other embodiments, the disinfection device A can be adapted for use in a variety of surface applications such as disinfecting counters, sinks, kitchen surfaces, bathroom surfaces, and more.

The disinfection device A can disinfect volumes of water or other liquid for personal consumption or other use by exposing microorganisms to the germicidal radiation of UV-C light. The UV-C spectrum ranges from wavelengths of 100 nm to 280 nm with the most effective germicidal range of UV-C between 200 nm and 280 nm. Photons in this germicidal wavelength range are energetic enough that the photons striking the nucleus of the microorganism, break the base pairs in its helical strand of DNA, thus causing the formation of pyrimidine dimers. As a result, the broken DNA can no longer be replicated, disabling cell division, and protein manufacturing, i.e. eliminating the microorganism's ability to reproduce, therefore, removing the risk of infection.

Figure 8:
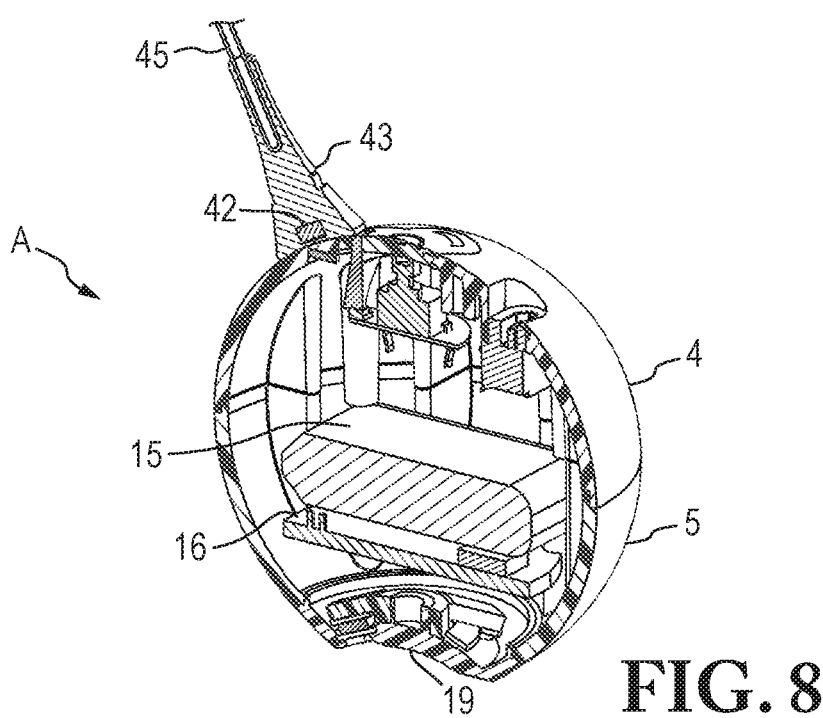
FIG. 8 is a cross-sectional view along I-I of FIG. 1 showing the entire disinfection device of FIG. 7, with the addition of the tactile switch, rubber power button, switch and indicator LED PCB, indicator LED, indicator LED light pipe, waterproof micro USB, ferromagnetic plate, magnetic retrieval connector, small connector cord, and magnet.
Figure 9:
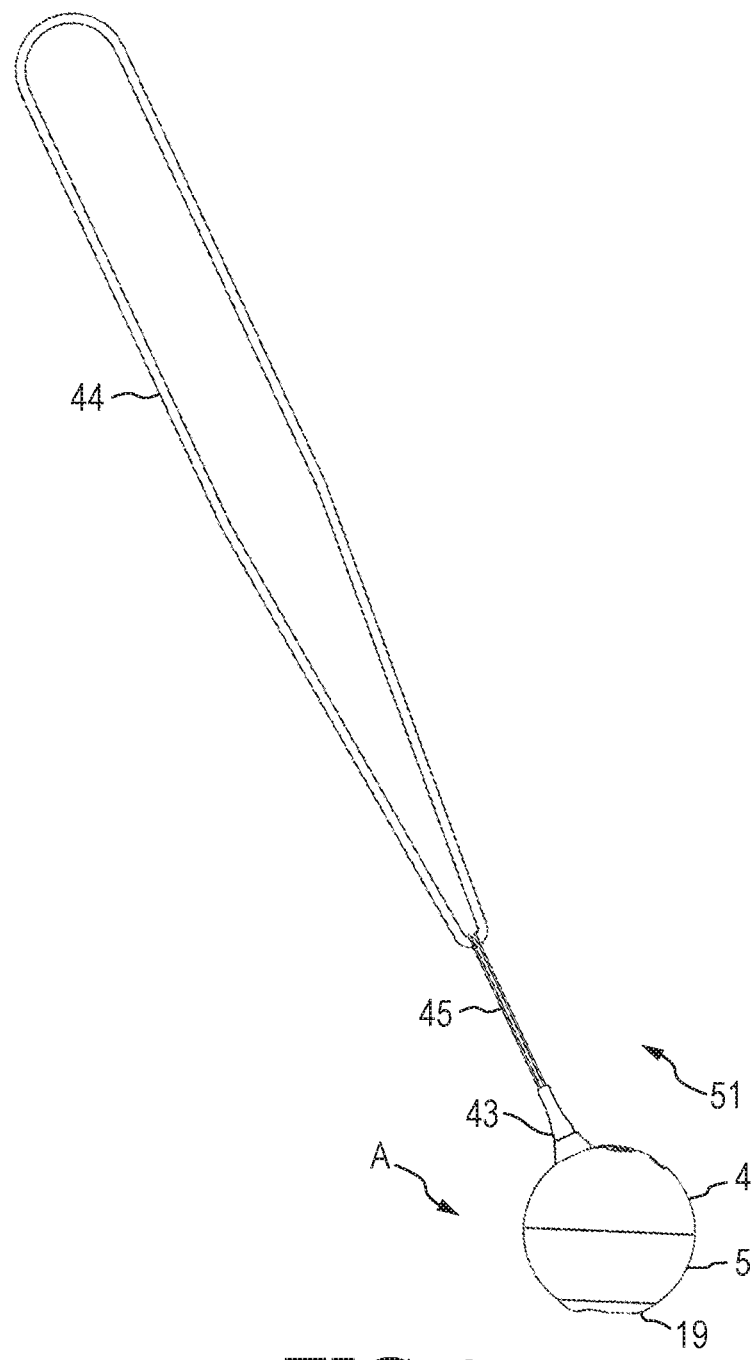
FIG. 9 is a perspective side view of the retrieval lanyard attached to the disinfection device.
Figure 10:
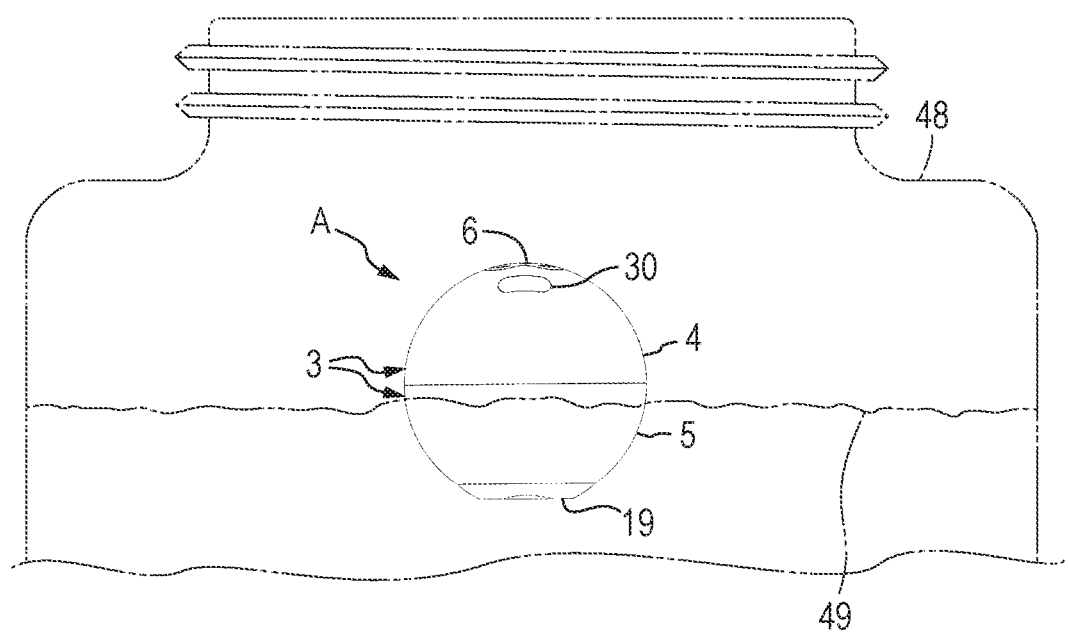
FIG. 10 is a perspective view of the disinfection device floating in water with the UV-C LED array facing downward.

As shown in FIGS. 1-10, the invention is a portable, consumer electronic disinfection device A equipped with UV-C LED 1 mounted in an array 2 that can be immersed in water contained in a vessel 48 (FIG. 10). The disinfection device A has an outer housing 3 to protect the internal components. Mounted to the lower hemisphere 5 of the outer housing 3 of the disinfection device A is the UV-C LED array 2. Mounted to the upper hemisphere 4 of the disinfection device A is a rubber power button 6, a waterproof micro USB 8, indicator LED(s) 9, tactile switch 11, ferromagnetic plate 14, indicator LED light pipe 10, and switch and indicator LED PCB 12. The rubber power button 6 and tactile switch 11 are positioned so as to be accessible from the outside of the upper hemisphere 4. As shown in FIG. 10, the disinfection device A floats in water 49 that can be contained in a vessel 48. The internal components are situated such that the heaviest internal components sit in the lower hemisphere 5 of the disinfection device A making the entire disinfection device A bottom heavy while maintaining a positive buoyancy overall. This automatically orients or rights the disinfection device A so that the UV-C LED array 2 faces in a general downward direction. This is a self-righting feature.

The disinfection device A is programmable. A user selects a time dose of radiation from the ultraviolet-C emitting (UV-C) light emitting diode(s) (LEDs) 1 to render pathogen containing water 49 safe for human consumption. The programming allows the user to regulate the dose of UV-C required to achieve sufficient disinfection of the volume of water 49 being treated.

Feature Set:

Floating/Self-Righting

The disinfection device A is designed to float at the top of the water 49 it is being deployed in. The weight distribution of internal components is centered and concentrated toward the lower hemisphere 5 containing the UV-C LED array 2, allowing the disinfection device A to automatically right itself. This gives the disinfection device A, a natural vertical orientation, with the UV-C LEDs 1 pointing in the nadir (downward) direction. This is desirable to ensure that the UV-C LEDs 1 emit their UV-C radiation downward into the entire volume of water for disinfecting.

Waterproof

The disinfection device A complies with the IP67 Guidelines for moisture and fine particulate protection. The disinfection device A uses a water tight sealing method for coupling the upper hemisphere 4 to the lower hemisphere 5 creating a water tight outer housing 3.

In other embodiments, the waterproof nature of the disinfection device A may be more or less robust depending on the specific needs of that embodiment's application.

Lightweight

For the current embodiment of the design, the weight of the disinfection device A will be such that the disinfection device remains buoyant in water.

In other embodiments of the design it can be conceived that the disinfection device could have a negative buoyancy or neutral buoyancy in water as well.

Size Considerations

In the current embodiment of the design the total outside diameter of the disinfection device A should preferably be equal to or less than 2 inches for personal water bottle use, with target consumer ready designs aiming in the range of 1.75 in to 1.25 in. This permits the disinfection device to fit through most wide mouth water bottles, water bladders, and a select number of bottles with smaller mouth openings.

Typical Bottle Opening Dimensions:

Largemouth Nalgene Bottle: 2.1" diameter opening

Camelbak reservoir opening: 2.5"-3" diameter opening

Camelbak bottle opening: 2" diameter opening

In other embodiments of the design, the disinfection device's A overall size can be fully scalable up or down to meet the requirements of any liquid/water disinfection application.

Lifespan

The life span of the disinfection device will be limited by the recharge capacity of the lithium ion polymer batteries. The life span of the rechargeable battery 15 in the current embodiment of the design is estimated to be 600 recharge cycles translating to approximately 9,000 run cycles. This translates to roughly 525 hours of operational life when the battery is fully discharged and then recharged. Under these conditions the disinfection device will last the average outdoors adventurer and international traveler approximately 450 years with an estimated average of 30 days of use per year.

If the user is using the disinfection device A twice a day to produce the minimum suggested healthy amount of water for an individual's consumption, the disinfection device's A life span can be calculated to approximately 12 years.

Radiation Hardness

The disinfection device itself is an electromagnetic radiation emitting device and can withstand electromagnetic radiation emission within the visible and UV spectrum ranging from UV-C at 200 nm up to visible spectrum 700 nm.

Outer Housing

The disinfection device A has an outer housing 3 that, in a first embodiment of the invention, approximates a sphere in appearance and shape. The purpose of the outer housing 3 is to provide a durable, protective outer casing that can serve as a mounting structure for all of the external and internal components to be secured to, as well as function as durable shock resistant protection for the internal components.

The outer shell can be made from any food safe, non-oxidizing, non-UV reactive, water insoluble, hydrophobic materials that are also shock resistant and shatter proof at temperatures between −30c to 110c. The outer housing 3 material is preferably food safe conforming to the ANSI standards for food safe materials. Some suitable materials considered for the design are, but are not limited to, plastics such as food grade polypropylene (PP), food grade Acrylonitrile butadiene styrene (ABS) with a UV cap, and food grade Tritan, as well as any suitable food grade metals, and any food grade composite materials. The outer housing 3 may also be made of one or more of the proposed materials used in combination, or any suitable material.

The design of the external surface and overall geometry of the outer housing 3 is generally spherical in nature or bounded by any type of geometric surfaces that together approximate a spherical exterior. The advantage of using a spherical type shape is that the disinfection device A can be deployed in most applications without the worry of conflicting geometries of the deployment container. In other embodiments of the invention the outer housing 3 can be any appropriate geometric shape, combination of shapes or amorphous design. Other shapes may include any geometric shape that can fit through the opening of a desired container.

The outer housing 3 has both an upper hemisphere 4 and a lower hemisphere 5 as shown in FIGS. 7, 8, 9, 10, 11. The interior of the outer housing 3 is mostly hollow with the exception of the internal electrical components and requisite structural features and mounting posts.

The upper hemisphere 4 of the outer housing 3 contains a pattern of multiple structural ribs 26 that protrude from the inner wall of the upper hemisphere 4 towards the interior of the disinfection device A. These structural ribs 26 serve as braces for securing the rechargeable battery 15 from shifting forward and backward as well as side to side. In addition, the structural ribs 26 serve as structural supports increasing the rigidity of the outer housing 3 as well as functioning as clocking features 29 for assistance in lining up the two hemispheres 4 & 5 during manufacturing and assembly of the disinfection device A. For purposes of this invention, the term clocking feature is any structural feature that facilitates the lining up of parts during manufacturing. The upper hemisphere 4 also contains multiple rechargeable battery mounting posts 28 that extend from the inner surface of the upper hemisphere 4 down towards the rim where the upper hemisphere 4 and lower hemisphere 5 meet. These rechargeable battery mounting posts 28 are designed to secure the rechargeable battery 15 from shifting up and down within the disinfection device A when assembled.

In addition, the upper hemisphere 4 contains and defines features and relief cuts for over molding the rubber power button 6 into the upper hemisphere 4. These features and relief cuts include a main rubber power button cut out 33 that provides space for over molding the rubber power button 6 into the upper hemisphere 4, a rubber power button over molding lip 34 that is located around the periphery of the rubber power button cut out 33 that provides additional surface area for the over molded material to adhere to, and several over molding rubber power button securing holes 35 that serve to prevent the rubber power button 6 from separating from the upper hemisphere 4 when depressed repeatedly.

Further, the upper hemisphere 4 contains a switch and indicator LED PCB mounting post 27 for securing the switch and indicator LED PCB 12 to the upper hemisphere 4, a ferromagnetic plate cut out 32 for mounting the ferromagnetic plate 14 to the upper hemisphere 4. The lower hemisphere 5 has a lower hemisphere mounting flange 41 (FIG. 5) for adhering to the upper hemisphere 4 by connecting to the upper hemisphere mounting flange 31 of the upper hemisphere 4 during assembly of the disinfection device A. The mounting flanges 31 and 41 are complimentary and create a locking engagement when connected.

The lower hemisphere 5 of the outer housing 3 contains a pattern of multiple structural ribs 36 that protrude from the inner wall of the lower hemisphere 5 towards the interior of the disinfection device A. These structural ribs 36 serve as braces for securing the rechargeable battery 15 from shifting forward and backward as well as side to side. In addition, the structural ribs 36 serve as structural supports increasing the rigidity of the outer housing 3 as well as functioning as clocking features 39 for assistance in lining up the two hemispheres 4 & 5 during manufacturing and assembly of the disinfection device A. The lower hemisphere 5 also contains multiple rechargeable battery mounting posts 38 that extend from the inner surface of the lower hemisphere 5 up towards the rim where the upper hemisphere 4 and lower hemisphere 5 meet. These rechargeable battery mounting posts 38 are designed to secure the rechargeable battery 15 from shifting up and down within the disinfection device A when assembled.

Figure 4:
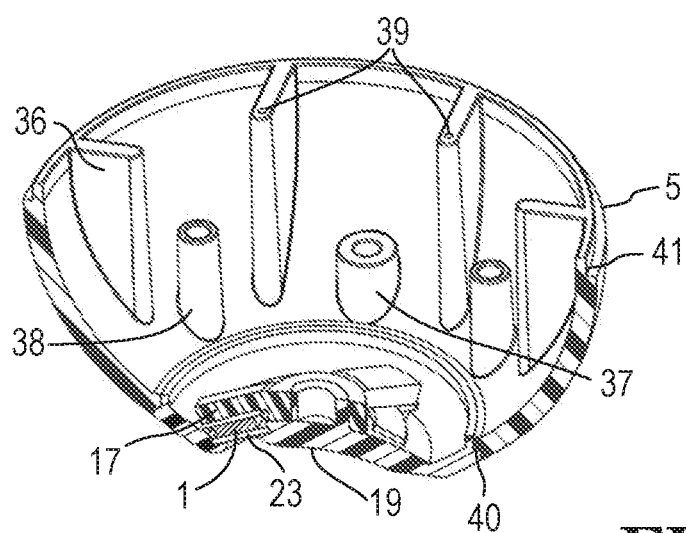
FIG. 4 is a cross-sectional view of the lower hemisphere showing the UV-C LED heatsink faceplate, flexible PCB, UV-C LED, fused silica windows and UV-C LED heatsink bracket and the lower hemisphere's internal fastening features, including structural ribs, (two of four) rechargeable battery mounting posts and a single main PCB mounting post and the upper hemisphere mounting flange cut away located around the rim of the lower hemisphere.
Figure 5:
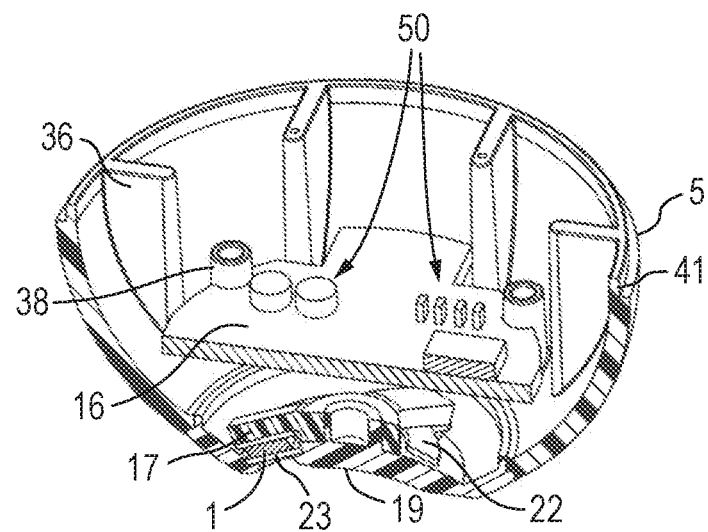
FIG. 5 is a cross-sectional view of the lower hemisphere as shown in FIG. 4 and showing the main PCB in position, mounted to the main PCB mounting post.

In addition, the lower hemisphere 5 contains multiple main PCB mounting posts 37 that are designed to serve as mounting and securing features for the main PCB 16 (FIGS. 4 and 5).

The lower hemisphere 5 also contains a lower hemisphere mounting flange cut away 41 at its upper rim to engage with the upper hemisphere mounting flange 31 located on a lower rim of the upper hemisphere 4.

Further, the lower hemisphere 5 defines a cut out for receiving the UV-C LED heatsink face plate 19. This cut out provides the lower hemisphere 5 with the heatsink faceplate mounting lip 40 that is designed to provide additional surface area for proper adhesion between the UV-C LED heatsink faceplate 19 and the lower hemisphere 5 during assembly of the disinfection device A.

UV-C LEDs 1 for Germicidal Efficacy

The purpose of the UV-C LEDs 1 in the current embodiment of the design is to efficiently emit Ultra Violet electromagnetic radiation within the germicidal range of the Ultraviolet-C spectrum, more specifically to emit electromagnetic radiation at or around the wavelength($\lambda$) range of 270 nm to 280 nm for purposes of disinfection.

Suitable LEDs include gallium nitride (GaN) semiconductor LEDs which can be designed to produce sufficient power output to achieve the same disinfection efficacy as mercury lamps, but with fewer drawbacks. The LEDs currently on the market come in various package designs with some packaged surface mount units as small as 3 mm×3 mm square. These UV-C LEDs also have a significantly longer lifespan, with some units reaching greater than 10,000 hours of operation. In addition, UV-C LEDs have a lower operating power requirement than their mercury lamp predecessors.

TABLE 1

UV Dose Requirements (mJ/cm2) for Pathogen Inactivation
Target Pathogen

| | Log Inactivation | | | | | | | |
|---|---|---|---|---|---|---|---|---|
| | 0.5 | 1.0 | 1.5 | 2.0 | 2.5 | 3.0 | 3.5 | 4.0 |
| Cryptosporidium UV dose requirement | 1.6 | 2.5 | 3.9 | 5.8 | 8.5 | 12 | 15 | 22 |
| Giardia UV dose requirement | 1.5 | 2.1 | 3.0 | 5.2 | 7.7 | 11 | 15 | 22 |
| Virus UV dose requirement | 39 | 58 | 79 | 100 | 121 | 143 | 163 | 186 |

Source: Basis for Acceptance of NSF/ANSI Standard 55 Class "A" Ultraviolet Disinfection Equipment for Use in Small Public Water Systems in Colorado Department of Public Health and Environment Water Quality Control Division Engineering Section, March 2013.

The minimum UV-C dose required of the disinfection device A is a dose of 40 mJ/cm2. Based on subsequent findings and design consideration, the dose parameters and other design parameters have been scaled based on the design choice dose of 40 mJ/cm2.

UV-C LED Array 2

The purpose of the UV-C LED array 2 in the current embodiment of the design is to create as close to a uniform emission pattern as possible, by overlapping the UV-C light that is emitted from each of the UV-C LEDs 1.

Figure 20:
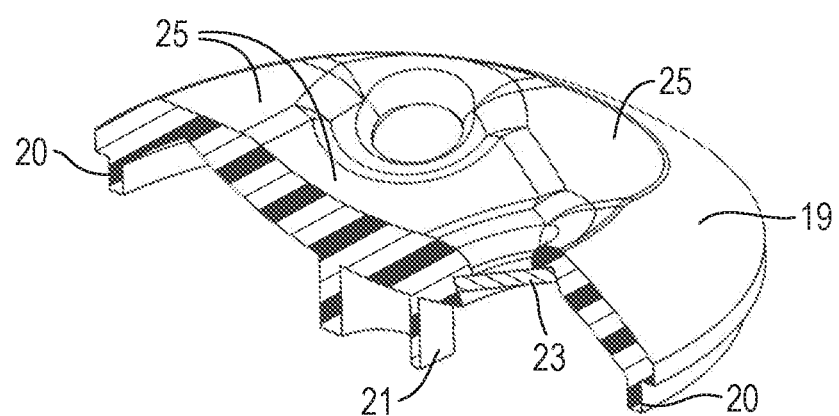
FIG. 20 is a cross-sectional view along section line X-X of FIG. 19 of the UV-C LED heatsink faceplate with the fused silica window in place and showing the angle of the UV-C LED's radiometric emission pattern and the concave design of the UV-C LED heatsink faceplate with UV-C LED light emittance relief cuts.

UV-C LEDs 1 are mounted in the UV-C LED heatsink faceplate 19 that is contained in the lower hemisphere 5 of the disinfection device A. This UV-C LED heatsink faceplate 19 has a concave outer surface as shown in the cross-section view of FIG. 20. allowing the UV-C LEDs 1 to be mounted internally around the rim of the concave surface, so as to project their UV-C light out and across the concave surface, thus overlapping with the UV-C light being emitted from their counterparts across from them. This configuration considers the viewing angle for each UV-C LED 1 of ~130°, and is desirable to mitigate the occurrence of emittance gaps in the UV-C emission pattern produced by the UV-C LED array 2.

Radiometric Emissions and Emission Pattern

Based on the specifications of the UV-C LEDs 1 chosen for this embodiment of the design, each UV-C LED 1 provides an output power ranging from 2 to 4 mW with 4 mW being emitted at the manufacturer suggested drive current of 150 mA, and a voltage drop of 7.0 V. The current embodiment of the design envisions the use of three UV-C LEDs 1 to be driven simultaneously, thus providing a total optical power output of approximately 12 mW of UV-C radiation.

To achieve the desired log base reduction of the pathogens contained in the volume of water being treated a UV-C dose of 40 mJ/cm$^2$ is required.

$$\text{Dose(mJ/cm2)} = \text{UV intensity(mW/cm2)} * \text{Time(s)}$$

The following device power output, water sample conditions and vessel geometry example is assumed typical for the application:

3 UV-C LEDs in assembly
   providing 12 mW of UV-C illumination,
   illuminating a circular area with diameter of 90 mm
   corresponding to downward illumination from the top of a 32-oz. bottle
   into water with low turbidity.

Thus, the area to be uniformly illuminated is calculated as:

$$A(\text{cm2}) = \pi(45 \text{ mm})2 = \pi(4.5 \text{ cm})2 = 63.6 \text{ cm2}$$

To achieve the design dose of 40 mJ/cm2 when supplying 12 mW of UV-C illumination, it is calculated that the UV-C LED 1 intensity and exposure time required will be as follows:

$$40 \text{ mJ/cm2} = [12 \text{ mW} \times T(s)]/63.6 \text{ cm2}$$

Solving for the exposure time T(s) we find:

$$T(s) = [63.6 \text{ cm2} * 40 \text{mJ/cm2}]/12 \text{ mW}$$

$$T(s) = 212 \text{ s or } 3.5 \text{ minutes}$$

This UV-C dose time will be applied to the run cycle selection providing users the ability to select this option as well as two additional run cycle time options designed to account for additional typical volumes of water.

In other embodiments of the design the run cycle times can be any length of time needed for a specific application and device specifications.

UV-C LED Heatsink Faceplate and UV-C LED Heatsink Bracket Assembly

Figure 12:
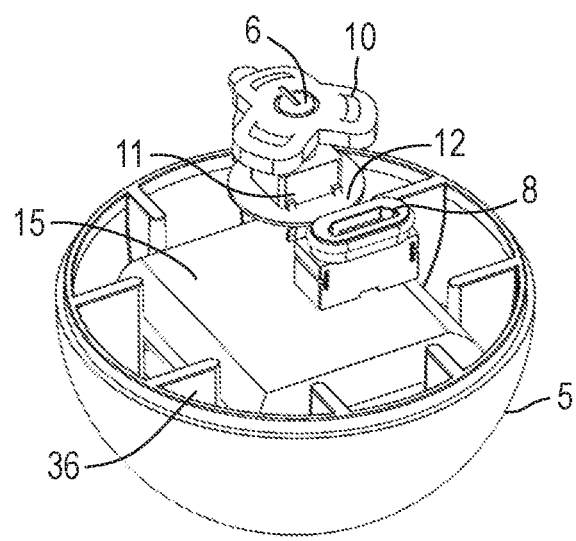
FIG. 12 is a perspective view of the lower hemisphere showing the internal components, namely the rubber power button, indicator LED light pipe, tactile switch, waterproof micro USB, switch and indicator LED PCB, and the lower hemisphere with the rechargeable battery in its mounted position.
Figure 13:
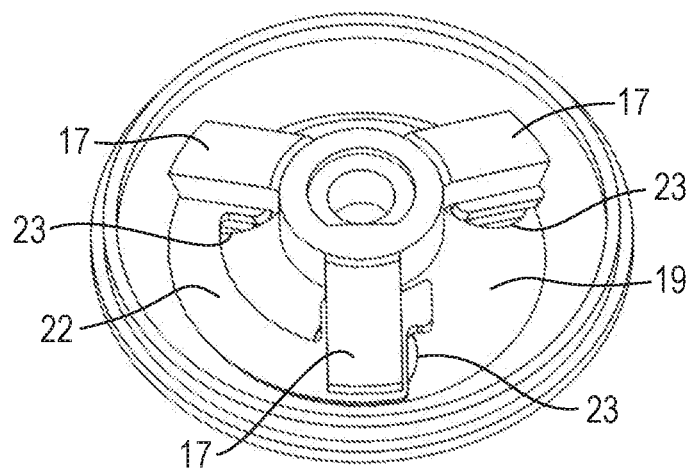
FIG. 13 is a perspective view of the UV-C LED heatsink faceplate assembly that depicts the UV-C LED heatsink faceplate with UV-C LED heatsink bracket, flexible PCB, UV-C LED and fused silica windows.
Figure 14:
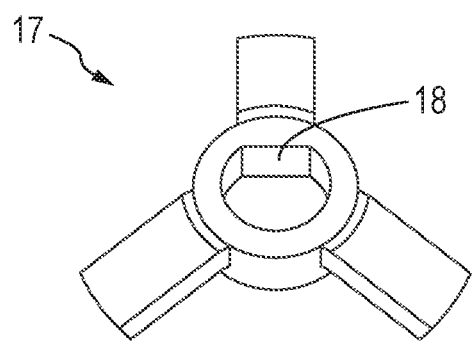
FIG. 14 is a perspective view of the UV-C LED heatsink bracket with the UV-C LED heatsink bracket clocking cut out visible.
Figure 15:
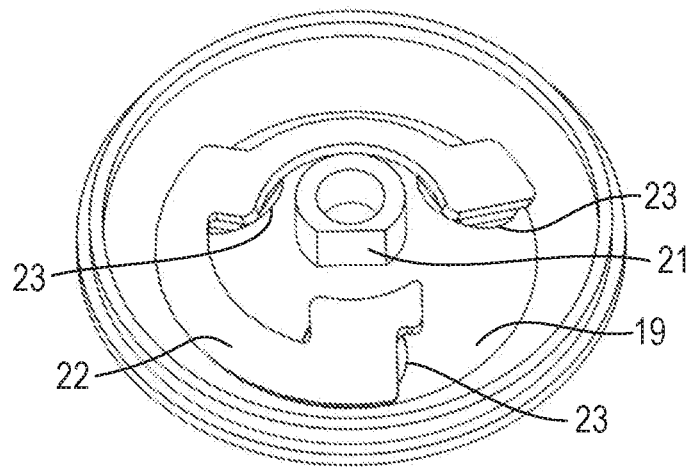
FIG. 15 is a perspective view of the UV-C LED heatsink faceplate assembly that depicts the UV-C LED heatsink faceplate with flexible PCB, UV-C LED and fused silica windows.
Figure 16:
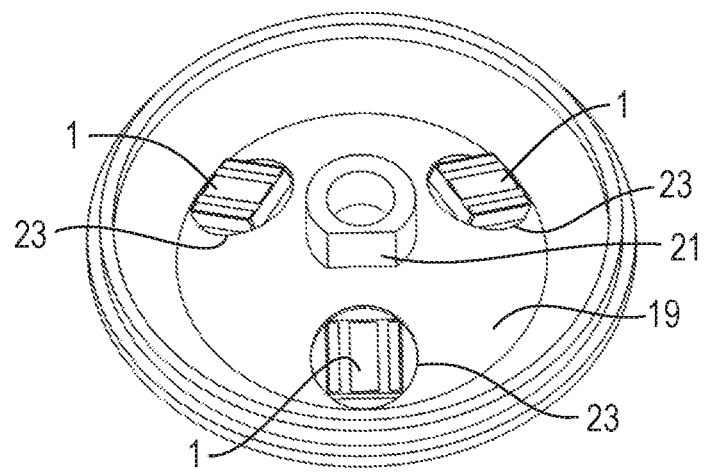
FIG. 16 is a perspective view of the UV-C LED heatsink faceplate assembly that depicts the UV-C LED heatsink faceplate with UV-C LED and fused silica windows.
Figure 17:
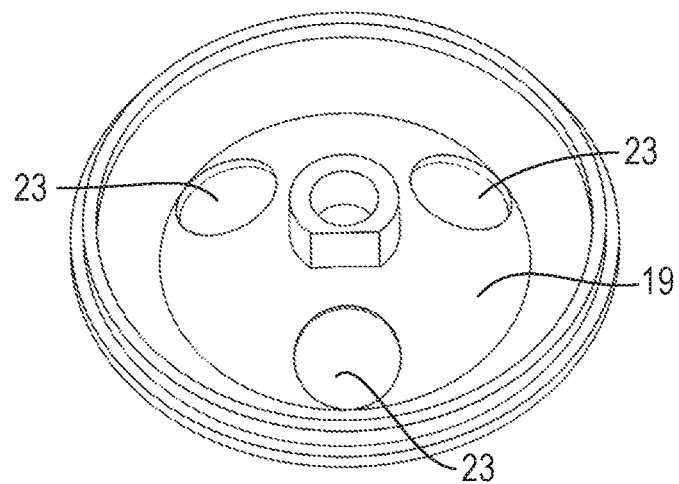
FIG. 17 is a perspective view of the UV-C LED heatsink faceplate assembly that depicts the UV-C LED heatsink faceplate with fused silica windows.
Figure 18:
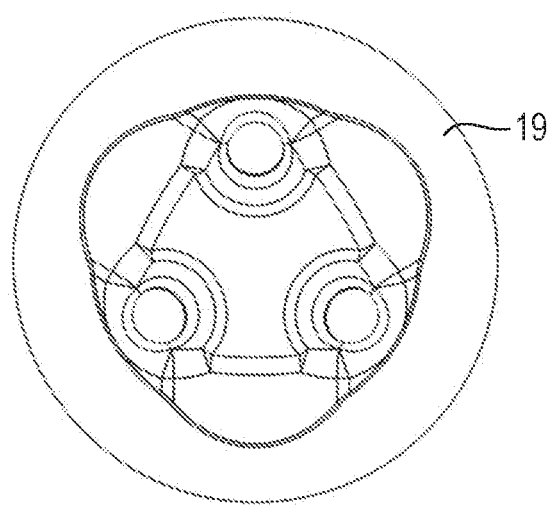
FIG. 18 is a perspective view of the outward facing surface of the UV-C LED heatsink faceplate showing the contour lines derived from the curvature of the outside surface of the UV-C LED heatsink faceplate.
Figure 19:
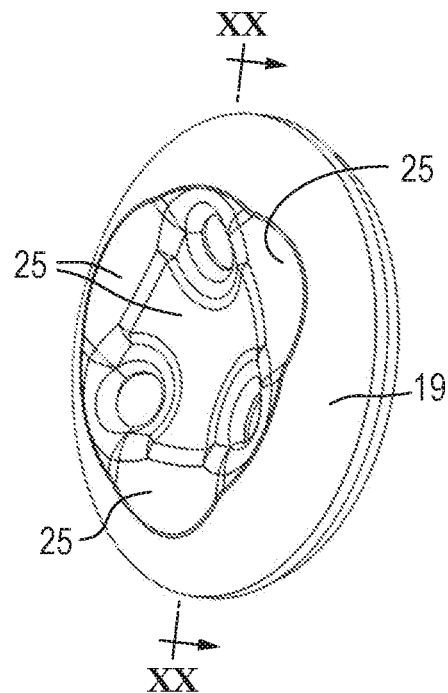
FIG. 19 is a perspective view of the side of the UV-C LED heatsink faceplate.

The UV-C heatsink face plate and heatsink bracket are shown in FIGS. 12-21. The UV-C LED heatsink faceplate 19 and UV-C LED heatsink bracket 17 assembly, in the preferred embodiment of the design, as seen in FIGS. 13 and 14 is implemented to draw heat away from the UV-C LEDs 1 and dispel that heat into the water that the disinfection device A is floating in during use and into the surrounding environment. In doing so the UV-C LED heatsink faceplate 19 and UV-C LED heatsink bracket 17 assembly serves to keep the UV-C LEDs 1 at their normal operating temperatures, thus ensuring that the UV-C LEDs 1 do not degrade or fail during use.

The UV-C LED heatsink faceplate 19 will be aligned with the UV-C LED heatsink bracket 17 by aligning the UV-C LED heatsink bracket clocking cut out 18 and the UV-C LED heatsink faceplate clocking cut out 21, and allowing the UV-C LED heatsink bracket 17 to slip down over the center post of the UV-C LED heatsink faceplate 19.

The UV-C LED heatsink faceplate 19 is mounted in the lower hemisphere 5 of the disinfection device A in the area of the heatsink mounting flange 20. This UV-C LED heatsink faceplate 19 has a concave outer surface as shown in the cross-section view of FIGS. 19 and 20 allowing the UV-C LEDs 1 to be mounted internally around the rim of the concave surface at approximately a 60° angle to the flat plane created by the rim. In other embodiments, this angle may be adjusted to provide proper alignment of the emission pattern of any UV-C LEDs 1 being used. The UV-C LEDs 1 will be centered over the counter-bored holes cut into and defined by the back of the UV-C LED heatsink face plate 19. These holes will be sealed by adhering the fused silica windows 23 into the counter-bore holes with a UV stable organic compound such as silicone. The UV-C LEDs 1 will then be pressed against this fused silica window 23 allowing them to emit their UV-C light out through the fused silica window 23 and into the volume of water being treated. This embodiment is designed to take into account the viewing angle for each UV-C LED 1 of ~130°. By placing three UV-C LEDs 1 in an inward facing configuration within the UV-C LED array 2, and subsequently overlapping the UV-C emission pattern of each at a 60° tilt their UV-C light can be projected out and across the concave surface over the UV-C LED light emittance relief cuts 25, thus eliminating any gaps in the radiometric emission pattern of the UV-C LED array 2 as a whole.

In addition, the UV-C LED heatsink faceplate 19 may optionally have reflective surfaces surrounding the UV-C LEDs 1 to assist in radiometric dispersion.

In other embodiments of the design the UV-C LED array 2 can contain any number of UV-C LEDs 1 in any conceivable configuration lending to the proper emittance of their UV-C light onto or into the medium needing disinfection.

The thermal dissipation requirements of each UV-C LED 1 are such that the UV-C LED heatsink faceplate 19 and UV-C LED heatsink bracket 17 assembly draw, at minimum, one watt of heat away from each UV-C LED 1 of the disinfection device A. Any material is suitable for the heatsink faceplate and heatsink bracket that can perform this heat drawing function as well as provide proper support for the UV-C LEDs 1. The material must also have the property that it does not melt from the thermal emissions of the UV-C LEDs. In order to achieve this, and properly redirect the thermal build up out into the surrounding body of water the disinfection device A is floating in during operation, the UV-C LED heatsink faceplate 19 is coupled with the UV-C LED heatsink bracket 17.

The UV-C LED heatsink bracket 17 is mounted to the interior of the UV-C LED heatsink faceplate 19, making a thermally conductive contact with the flexible PCB 22, which is subsequently adhered to both the thermal pad and soldering pads of each of the UV-C LEDs 1. From there, the UV-C LED heatsink bracket 17 spans over the UV-C LEDs 1 making contact with the UV-C LED heatsink faceplate 19. This contact is necessary so that the heat from the operation of the UV-C LEDs 1 can be pulled away from each of the UV-C LEDs 1 through the thermal pads and redirected through the UV-C LED heatsink faceplate 19, then dissipated out into the body of water making contact with the outside of the UV-C LED heatsink faceplate 19.

In other embodiments of the design, proper thermal management of the interior components can be achieved through any method conceivable of dissipating enough heat away from the components that experience thermal buildup during operation.

The UV-C LED heatsink faceplate 19 can be made of aluminum or any suitable thermally conductive material that performs thermal dissipation such as, for example, copper, graphite and thermally conductive polymers.

In another embodiment, the entire housing or entire lower hemisphere material of the outer housing can be a heatsink itself wherein the heatsink faceplate is integral with the lower hemisphere. In this configuration, the entire lower hemisphere and faceplate that surrounds the UV-C LEDs will dissipate heat into surrounding water.

Rubber Power Button

Figure 11:
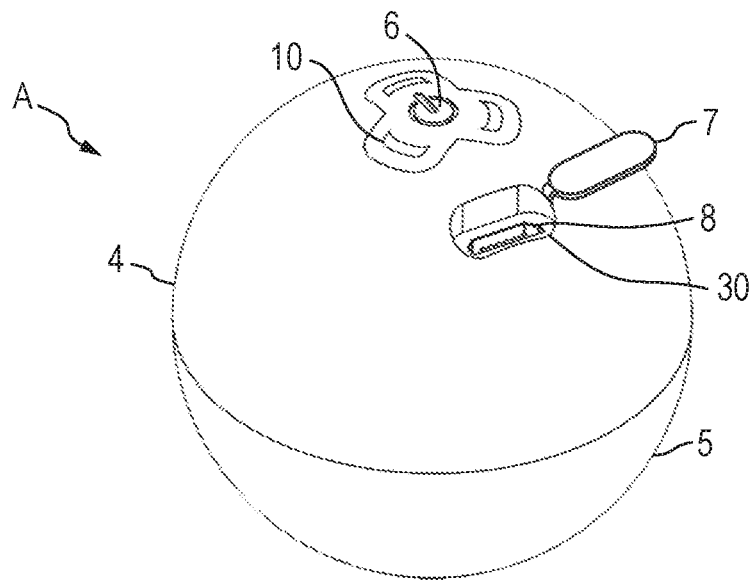
FIG. 11 is a perspective overhead view of the disinfection device showing the power button and USB port and USB cover.
Figure 22:
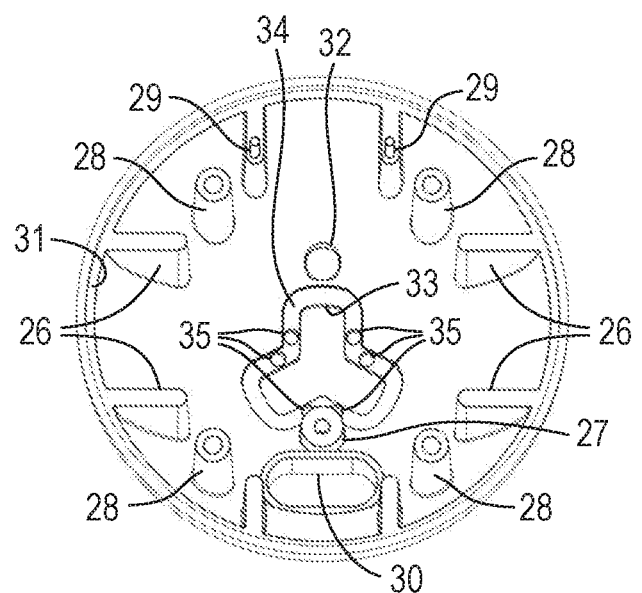
FIG. 22 is an upward facing perspective view of the inside of the upper hemisphere with no components in place.

FIGS. 2, 8 and 10-12 show the rubber power button 6 opposite from the UV-C LEDs on the disinfection device A. The rubber power button 6 seals the disinfection device A from water and particulate while providing the user access to the sub mounted tactile switch 11 (FIG. 12). The rubber power button 6 also provides a place for mounting the indicator LED light pipe 10 so that it can project the Indicator LED's 9 light through the upper hemisphere 4 of the outer housing 3 as shown in FIGS. 11 and 22. This is necessary so that the current mode of the disinfection device A is visible to the user.

Tactile Switch

As shown in FIGS. 12 and 22, the purpose of the tactile switch 11 is to provide the user with a way of controlling and initiating the different operational modes of the disinfection device A. The tactile switch 11 is a device that is soldered to the corresponding switch and indicator LED PCB 12 for electrical connection within the assembly. The tactile switch 11 is a depressible switch with tactile feedback that serves to provide electrical control signals to the main PCB 16 (power control board) containing the UV-C LED driver circuitry and device control circuitry. The user controls for the disinfection device A will be discussed in detail in the programming section below, but function to turn the disinfection device A on and off, put the disinfection device into a lock mode, display the remaining battery life of the unit, as well as selecting the run time of the UV-C LEDs 1 based on desired exposure and volume of water being treated.

The rubber power button 6 of one embodiment of the invention is an over molded water tight, soft, depressible, rubberized button with a Durometer rating between 20 oo and 80 D. In other embodiments of the invention, the power button may be anything that allows the user to input commands for the disinfection device A.

Indicator LED(s)

Figure 21:
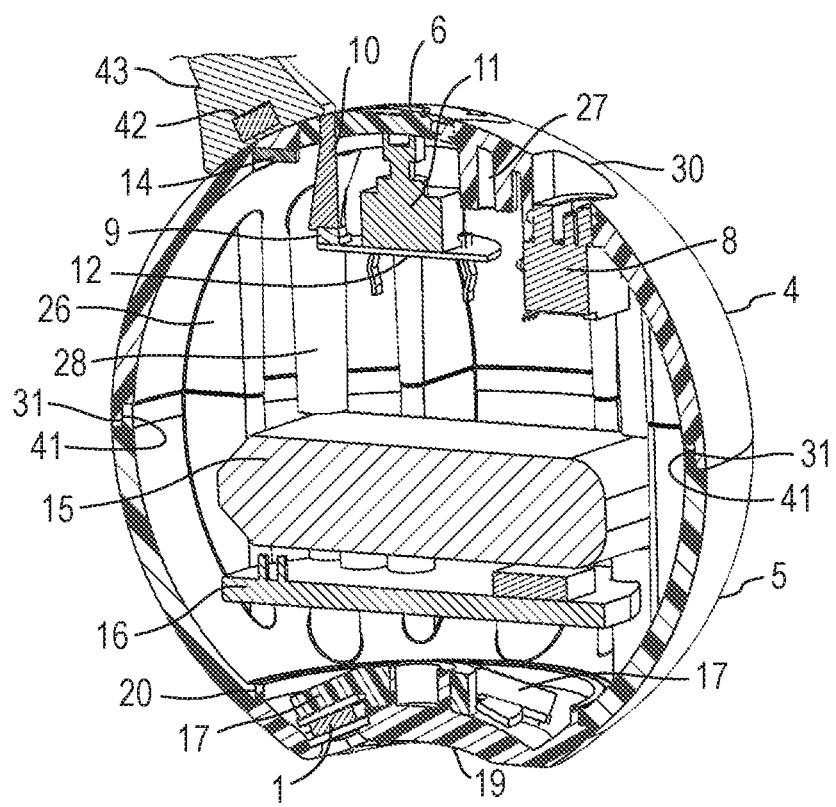
FIG. 21 is a cross-sectional view of the entire disinfection device with all the components in place.

The purpose of the indicator LED(s) 9, as shown in FIG. 21, is to provide the user with visual feedback of the disinfection device A; for example, designation of the current operational mode, run cycle initiation and battery life span, etc. The indicator LED 9 within the preferred embodiment of the invention is a small surface mounted, red, blue and green (RBG) LED.

In other embodiments, the indicator LED 9 can be any light source that provides a visual signal to the user of the disinfection device A.

Indicator LED Light Pipe

Figure 1:
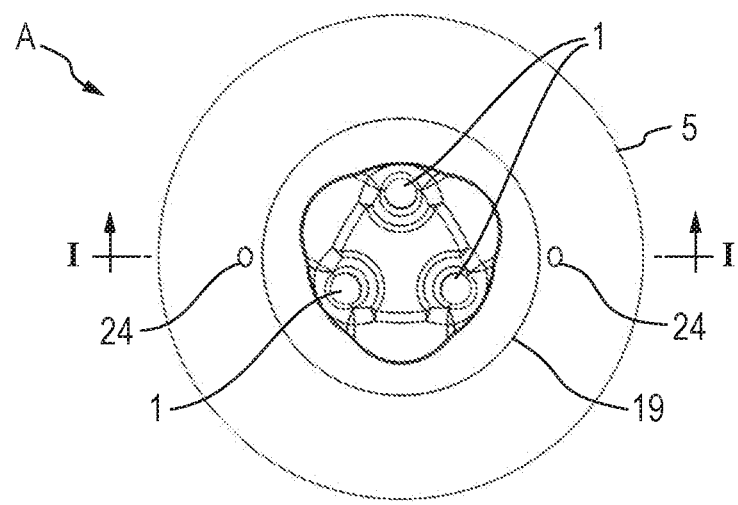
FIG. 1 is a perspective view of the lower hemisphere of the disinfection device showing the UV-C LED Array and UV-C LED heatsink faceplate (with tangent contour lines)
Figure 2:
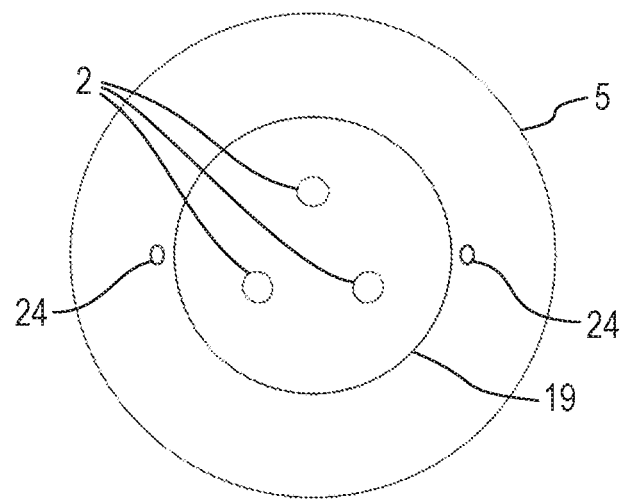
FIG. 2 is a perspective view of the lower hemisphere of the disinfection device showing the UV-C LED Array and UV-C LED heatsink faceplate (with no tangent contour lines)
Figure 3:
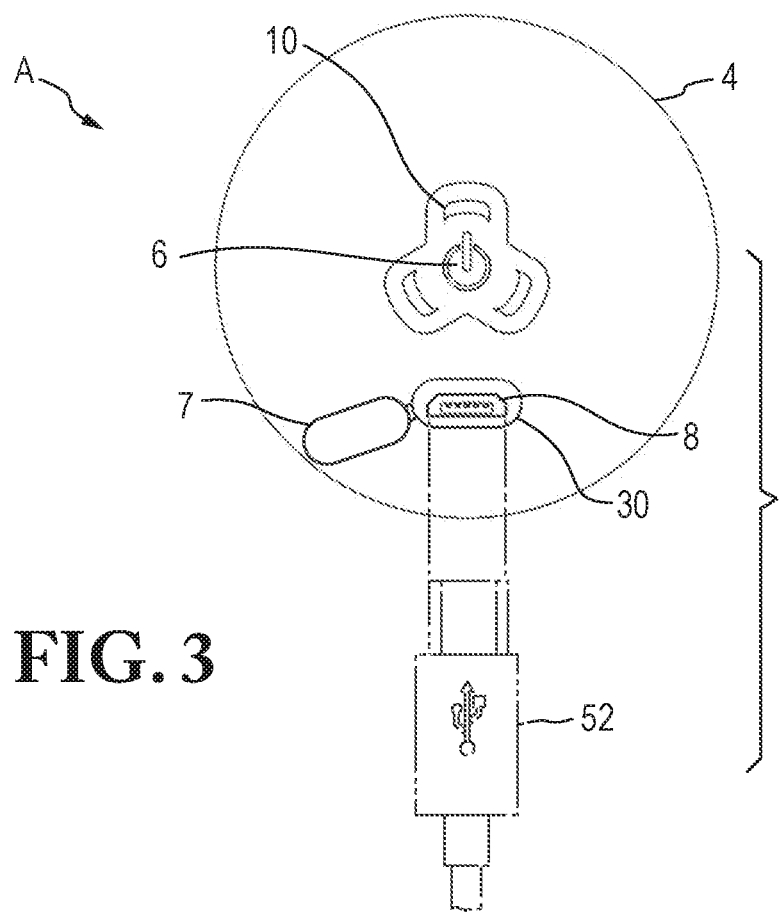
FIG. 3 is a perspective view of the upper hemisphere, the rubber power button, indicator LED light pipe, waterproof micro USB, micro USB mounting hole, micro USB cover and USB cable.

As shown in FIGS. 3 and 21, the LED light pipe 10 provides a pipe for transmitting the signal light from the indicator LED 9 through the upper hemisphere 4 of the outer housing 3. The indicator LED light pipe 10 is preferably a clear polymer formed into a shape that effectively transmits light from the indicator LED 9 sub mounted on the switch and indicator LED PCB 12 to the outer surface of the outer housing 3.

Main PCB

Figure 6:
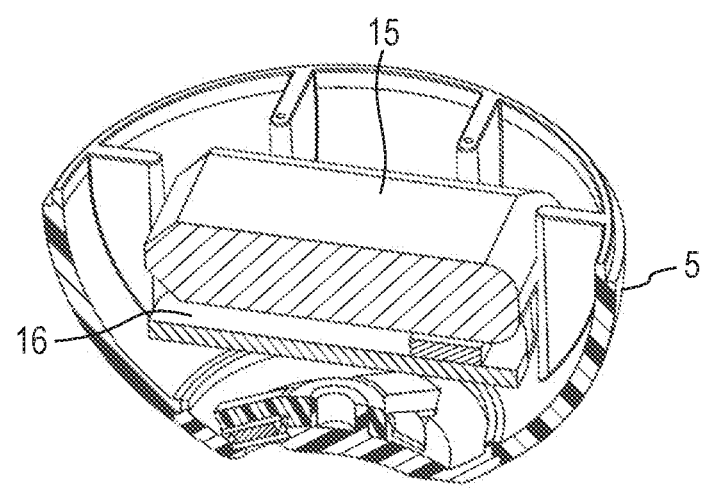
FIG. 6 is a cross-sectional view of the lower hemisphere as shown in FIG. 4 and FIG. 5 with the addition of the rechargeable battery in position, mounted to the rechargeable battery mounting posts.

As shown in FIGS. 5 and 6, the purpose of the main PCB 16 is to provide a mounting substrate for all of the disinfection device's A electrical components and circuitry 50. The circuitry provides operational control over the UV-C LEDs and all other electrical components. This is achieved through specific user input relayed to the device through depressing the rubber power button 6 and subsequently the tactile switch 11.

In other embodiments of the design, the Main PCB may contain any other componentry that provides a specific function for the disinfection device A.

Programming

As shown in FIG. 5, the control circuitry 50 mounted to the Main PCB 16 is programmed with firmware or software that will both allow the user to select from a variety of desired modes of operation, as well as allow the disinfection device A to relay operational feedback to the user. Users may designate the desired mode of operation by inputting command signals through the depression of the rubber power button 6 and subsequently the sub mounted tactile switch 11. As the tactile switch 11 is depressed in the predesignated patterns, the control circuitry will interpret the commands and initiate the corresponding operations. If the disinfection device A receives non-user input from the water sensing electrodes 24 or driver circuitry on the main PCB 16, then the disinfection device A will display the corresponding information to the user through the indicator LED(s) 9 and subsequently the indicator LED light pipe 10.

The different user selectable operational modes may be one or several UV-C LED run cycles, a lock mode, on and off power modes, and remaining battery capacity display mode. The firmware will also be able to initiate multiple safety modes designed to prevent improper use of the disinfection device A.

The user selectable run cycles are determined by the recommended effective dose needed for a given volume of water to be disinfected. This also allows the user to target specific volumes of water for disinfection.

Run Cycle Selection

An example of run cycle selection is to set a short run time. In this case, the user depresses the rubber power button 6 once, the indicator LED 9 will then flash blue once, indicating "short" or "setting one", three seconds later, the indicator LED 9 will light up continuously in blue for thirty seconds indicating that the disinfection device A is ready to be placed into the volume of water needing disinfection. At the end of the run cycle, the indicator LED 9 will intermittently flash green to indicate a successful run cycle was completed.

Another example of run cycle selection is to set a medium run time. In this case, the user depresses the rubber power button 6 twice, the indicator LED 9 will then flash blue twice, indicating "medium" or "setting two", three seconds later, the indicator LED 9 will light up continuously in blue for thirty seconds, indicating that the disinfection device A is ready to be placed into the volume of water needing disinfection. At the end of the run cycle, the indicator LED 9 will intermittently flash green to indicate a successful run cycle was completed.

Another example of Run Cycle selection is to set the long run time. In this case, the user depresses the rubber power button 6 three times, then the indicator LED 9 will flash blue three times indicating "long" or "setting three", three seconds later, the indicator LED 9 will light up continuously in blue for thirty seconds indicating that the disinfection device A is ready to be placed into volume of water needing disinfection. At the end of the run cycle the indicator LED 9 will intermittently flash green to indicate a successful run cycle was completed.

Lock Mode

The firmware will also allow the disinfection device to be placed in a lock mode that can be turned on and off. The lock mode will help to save power consumption and prevent un-wanted initiation of a run cycle. For example, to put the disinfection device into lock mode, the user depresses the rubber power button for six seconds or until the indicator LED 9 flashes four times and then remains off. When in lock mode, if the rubber power button 6 is bumped, the indicator LED 9 will flash blue four times and keep the disinfection device A in lock mode. To exit lock mode, the user will depress the rubber power button 6 for six seconds or until the indicator LED 9 flashes twice indicating that the disinfection device A has been taken out of lock mode. Once taken out of lock mode, normal run cycle selections can once again be made.

The firmware permits the user to determine the remaining battery life while the disinfection device A is in lock mode. When in lock mode the rubber power button 6 may be double-tapped to display the remaining battery life through the indicator LED 9 and the indicator LED light pipe 10. The remaining battery life will be displayed through different color designations that correspond to approximate battery life percentages remaining. The color green will designate 70%-100% battery life remaining, yellow will designate 30%-69% battery life remaining, and red will designate below 30% battery life remaining.

Safety Modes

The firmware will also enable the disinfection device A to provide the user with operational feedback as it pertains to the safe operation of the disinfection device A. If the firmware registers a signal from the water sensing electrodes 24 dictating that they have experienced a break in the impedance signal, this will be interpreted by the firmware to mean that the disinfection device is no longer submerged. The firmware will then initiate a run cycle stop, thus ensuring that the disinfection device A does not emit UV-C radiation into open air. In the preferred embodiment of the design, the interruption in signal from the water sensing electrodes 24 are displayed through the indicator LED(s) 9 and subsequently the indicator LED light pipe 10 as a red steady light. In other embodiments of the invention, this indication may be any predetermined designation.

If the firmware receives a signal that the driver circuitry registers a break in signal, whether by short or failure of any of the electronic components, this will be interpreted by the firmware to mean that the disinfection device is no longer operational and the firmware will initiate a disinfection device A shutdown, thus stopping the current run cycle or preventing a future run cycle from initiating. This will then be indicated to the user by displaying a rapid red flashing signal through the indicator LED 9 and subsequently the indicator LED light pipe 10.

The firmware in this embodiment of the design seeks to make using the disinfection device A as quick and easy as possible. Ideally, this can be envisioned as simply powering on the disinfection device A, selecting a desired run cycle then dropping the disinfection device A into the water. In other embodiments, the firmware can accommodate other configurations of electronic components and their uses.

Rechargeable Batteries

Figure 7:
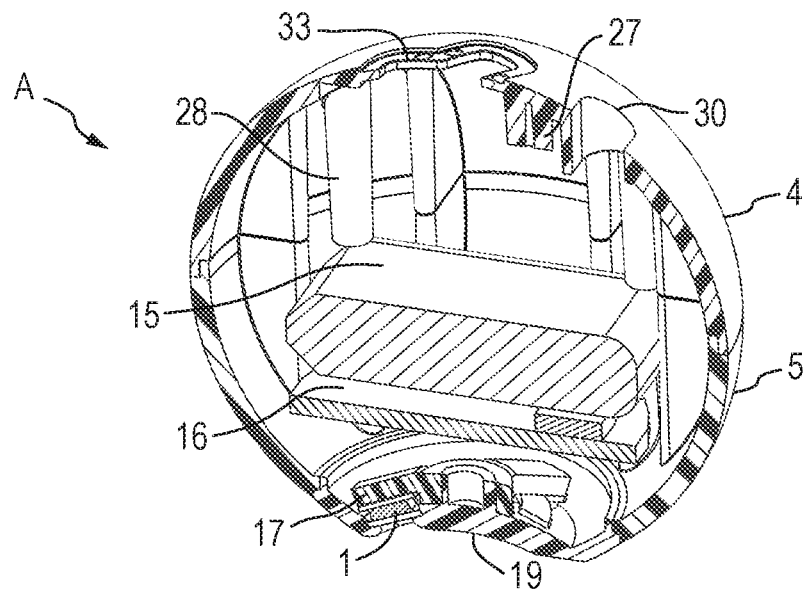
FIG. 7 is a cross-sectional view along line I-I of FIG. 1 showing the entire disinfection device with the upper hemisphere of the outer housing in place on the lower hemisphere of the outer housing.

As shown in FIGS. 6-8, the purpose of the rechargeable battery 15 is to supply the electrical components with the drive current and voltage required to properly operate. The rechargeable battery 15 is preferably a 3.7 v, 400 mAh lithium (Li) ion polymer battery. These batteries have a long recharging lifespan adding to the overall lifespan of the disinfection device A.

In other embodiments of the invention, the battery can be any standalone, rechargeable or non-rechargeable, power source that can be integrated into the design of the disinfection device A.

Power Consumption and Battery Life Consideration

Examples of batteries include Li-ion polymer batteries delivering a nominal 3.7 V each with a current ranging from 50 mA to 2000 mA each. The drive current needed through each of the UV-C LEDs will be 150 mA as specified by the manufacturer. The individual LED power consumption is calculated as:

$$7\ V * 0.15\ mA = 1.05\ W$$

Thus, for a device incorporating 3 UV-C LEDs 1, the total power dissipation of the UV-C LEDs 1 will be:

$$1{,}050\ mW * 3\ LEDs = 3{,}150\ mW\ or\ 3.15\ W$$

To provide a UV-C dose of 40 mJ/cm2, the disinfection device containing 3 UV-C LEDs operating as described above with total optical output of 12 mW must operate for 212 s (0.05888 h). Thus, the battery capacity consumed per dose cycle can be estimated to be:

$$0.05888\ h * 450\ mA = 26.5\ mAh$$

Thus, taking a single 400 mAh rechargeable Li-ion battery as a design example, a single charge cycle of the batteries omitting the rest of the drive circuitry would provide an estimated:

$$400\ mAh / 26.5\ mAh = 15.2\ dose\ cycles\ per\ charge.$$

Waterproof Micro USB (Universal Serial Bus)

The purpose of the waterproof micro USB 8 within the invention, as shown in FIGS. 3, 11 and 12, is to provide a receptacle for connecting the disinfection device A to an external power source via a USB cable 52 that has the ability to recharge the rechargeable battery 15. The waterproof micro USB 8 is mounted to the upper hemisphere 4 of the disinfection device A in the micro USB mounting hole 30 so that it may be accessed from the exterior of the outer housing 3. The hole 30 is defined by the upper hemisphere 4. The waterproof micro USB 8 is protected from both water and debris by the micro USB port cover 7. This cover can be pressed into place over the waterproof micro USB 8, thus blocking the opening from filling with liquids and debris.

This waterproof micro USB 8 enables the user to recharge the disinfection device using any micro USB cable that can plug into an external power source. The external power supply can include, but is not limited to, wall plugs, auxiliary battery packs, solar powered rechargers, or any external power source that supplies power through a micro USB connection to the disinfection device A.

In other embodiments of the invention, different power supply plugin options may be employed and implemented to achieve the same results as the waterproof micro USB 8. Any suitable cord and plug configuration can be used to supply power to the disinfection device A.

Retrieval Lanyard

As shown in FIGS. 9 and 21, the purpose of the retrieval lanyard 51 is to provide a way for pulling the disinfection device A out of the container the disinfection device A was placed into for disinfection, or otherwise. FIG. 9 shows a retrieval lanyard 51 that is made of a lanyard loop 44, connector cord 45 and magnetic retrieval connector 43 and magnet 42. The retrieval lanyard 51 uses magnetic attraction to dock or link the magnet 42 contained in the magnetic retrieval connector 43 to the ferromagnetic plate 14 that is sub-mounted to the upper hemisphere 5. By using magnetic attraction to link the magnetic retrieval connector 43 to the ferromagnetic plate 14 and subsequently the outer housing 3 of the disinfection device A, the retrieval lanyard 51 provides enough pull to securely lift the disinfection device A upwards while still easily detaching from the outer surface of the disinfection device A.

Removal of the disinfection device A from the container is not required at the end of the disinfection cycle. The disinfection device A can remain in the container of water until the water is consumed and the container is ready to be refilled. When empty, the user simply tips the container over and dumps out the disinfection device A before refilling the container for the next UV-C exposure. The floating feature in this instance also makes it less likely that the user will draw the disinfection device A into their mouth while drinking as it will float against the upper teeth or lips of the user.

In other embodiments, the retrieval method can be achieved by any coupling of the disinfection device with another device that serves to allow the user to remove the disinfection device from the container.

Water Sensing Electrodes

The purpose of the water sensing electrodes 24 is to provide the disinfection device A with a way of sensing whether or not it is submerged in water. The water sensing electrodes 24 are a series of electrodes mounted to the outer surface of the outer housing 3 where they can properly make contact with water. Once a disinfection run cycle is initiated by the user, the firmware that controls the disinfection device A begins looking for feedback from the water sensing electrodes 24 indicating that the disinfection device is submerged. If submersion is sensed within the thirty second standby period the firmware will then initiate the user selected run cycle. If submersion is not detected, the firmware will deactivate the user selected run cycle and display a red flashing indication through the indicator LED 9 and indicator LED light pipe 10 denoting that no run cycle was completed. This feature has the function of safety. The first function of this sensor ensures that the UV-C light is not emitted in open air or onto the user's person. The secondary function serves to ensure that the full UV dose is received by the volume of water being disinfected, therefore achieving the proper log reduction of the microorganisms contained in the drinking water.

Other water immersion sensing features may include, but are not limited to, visual detection, whereby the refractive index of a surface is changed due to water contact on that surface, or by means of a material that can absorb water and subsequently produce a measurable change due to the absorption.

What is claimed is:

1. A portable disinfection device for liquid purification or disinfection comprising:
    a protective liquid proof outer housing that provides buoyancy, said outer housing having a downward facing heatsink faceplate with a concave outer surface, and wherein said heatsink faceplate comprises a thermally conductive heat dissipating material said heatsink faceplate having an array of UV-C LEDs sealingly mounted in cut outs thereon, said array of UV-C LEDs arranged on said heatsink faceplate to create an overlapping microorganism killing UV-C radiation emission pattern outward therefrom into said liquid to eliminate the occurrence of emission gaps; and
    a thermally conductive heatsink bracket behind said UV-C LEDs that thermally transfers heat from said UV-C LEDs to said heatsink faceplate, wherein said heatsink faceplate and said thermally conductive heatsink bracket draw heat away from the UV-C LEDs and transfers said heat into said liquid or surrounding environment keeping the UV-C LEDs at their normal operating temperature.

2. The disinfection device of claim 1, further comprising a battery within said housing, said battery providing power to the device.

3. The disinfection device of claim 2, wherein said battery is rechargeable.

4. The disinfection device of claim 3, further comprising a waterproof USB port for charging said rechargeable battery.

5. The disinfection device of claim 3, wherein said rechargeable battery is a lithium ion polymer battery.

6. The disinfection device of claim 1, wherein said UV-C LEDs have fused silica windows.

7. The disinfection device of claim 1, wherein said disinfection device is hands-free during floatation in said liquid.

8. The disinfection device of claim 1, wherein said device is liquid proof when entirely submersed in said liquid.

9. The disinfection device of claim 1, wherein said device is a substantially hollow sphere.

10. The disinfection device of claim 1, wherein the UV-C LEDs emit UV-C spectrum light in a germicidal wavelength from of 200 nm to 280 nm.

11. The disinfection device of claim 1, wherein said housing is a hydrophobic material that is food safe, non-oxidizing, non-UV reactive, water insoluble and that is shock resistant and shatter proof at temperatures between −30c to 110c.

12. The disinfection device of claim 1, wherein said device is self-righting in liquid with said one or more UV-C LEDs pointing downward in said liquid.

13. The disinfection device of claim 1, further comprising a power control board with operational circuitry that controls the functionality of the disinfection device, said functionality of the disinfection device comprising one or more of (a) power on and off, (b) timer, (c) power level, (d) sleep mode, (e) lock mode, (f) safety mode and (g) battery life span indication.

14. The disinfection device of claim 1, further including a power control button, wherein said power control button allows the user to input desired controls for operating the disinfection device.

15. The disinfection device of claim 14, wherein said power control button further comprises indicator LED lights.

16. The disinfection device of claim 14, wherein said power control button is an over molded water tight, soft, depressible, rubberized button with a Durometer rating between 20 oo and 80 D.

17. The disinfection device of claim 1, further including an indicator LED, wherein said indicator LED allows the user to see the current mode or setting of the disinfection device.

18. The disinfection device of claim 1, wherein said disinfection device comprises an upper hemisphere and a lower hemisphere that are sealingly engaged to enclose and protect internal components, said upper hemisphere having a power button and said lower hemisphere having said UV-C LEDs, said device being self-righting during floatation and wherein during floatation, said UV-C LEDs of said lower hemisphere face generally downward and said power button faces generally upward.

19. The disinfection device of claim 1, further comprising one or more water sensing electrodes near said heatsink faceplate.

20. The disinfection device of claim 1, wherein said heatsink faceplate has an outward reflective surface.

21. The disinfection device of claim 1, wherein said heatsink faceplate and said heatsink bracket draw at least one watt of heat away for each UV-C LED.

22. The disinfection device of claim 1, wherein said UV-C LEDs face downward and outward during floatation and emit light at an angle to a horizontal plane.

23. The disinfection device of claim 22, wherein said UV-C LEDs are three or more in number and said light emitted from each UV-C LED during floatation creates an inward overlapping light emission pattern with the other UV-C LEDs.

24. The disinfection device of claim 1, wherein said device can withstand electromagnetic radiation emission within the spectrum of from UV-C at 200 nm up to visible spectrum 700 nm.

25. The disinfection device of claim 1, further comprising one or more indicator LEDs to provide visual feedback from the disinfection device.

26. The disinfection device of claim 1, further comprising firmware or software that enables the device to provide a user with operational feedback from the device.

27. The disinfection device of claim 1, wherein said disinfection device is time and UV-C dose programmable.

28. The disinfection device of claim 1, further comprising one or more of Bluetooth capability, Wi-Fi card and accelerometers.

29. The disinfection device of claim 1, further comprising a lanyard for retrieving said disinfection device from said liquid.

30. The disinfection device of claim 29, wherein said housing has a magnetic plate and wherein said lanyard has a magnet that attracts said magnetic plate for retrieval of said disinfection device from said liquid.

31. The disinfection device of claim 1, wherein said disinfection device comprises one or more multiple modes of operation, said multiple modes of operation comprising: on and off mode, lock mode, battery life display mode, and safety mode.

32. A method of disinfecting an amount of liquid that is held in a container comprising the steps of:
   a. turning on the disinfection device of claim 1 so that said UV-C LEDs emit UV-C light into said liquid;
   b. inserting the disinfection device into the container of liquid to be disinfected; and
   c. permitting said UV-C light emission for a sufficient time to kill microorganisms in said liquid so that said liquid is disinfected.

33. The method of claim 32, wherein said vessel comprises: a personal water bottle, backpack bladder, and water jug.

34. A water disinfection kit packaged in association together comprising:
   a. the disinfection device of claim 4;
   b. a USB cable;
   c. a lanyard for tethering to said disinfection device.; and
   d. a case.

35. The water disinfection kit of claim 34, wherein said case comprises:
   one or more surface mounted flexible solar panels, said case for connecting to and charging said device.

36. A portable buoyant disinfection device for liquid purification comprising:
   a) a protective liquid-proof spherical outer housing comprising a lower hemisphere and an upper hemisphere that connect to form a water tight seal there between; said upper hemisphere having a first end and said lower hemisphere having a second end opposite to said first end; said outer housing further having an internal compartment defined by an internally facing wall of said outer housing; said internally facing wall having structural ribs and mounting posts thereon;
   b) a power control board mounted on said mounting posts and securely positioned between said structural ribs;
   c) a battery mounted on said mounting posts and securely positioned between said structural ribs, said battery powering said device;
   d) one or more UV-C LEDs;
   e) a heatsink faceplate and heatsink bracket mounted within said second end of said lower hemisphere, wherein said heatsink faceplate is thermally connected to the heatsink bracket and said heatsink bracket draws heat away from the UV-C LEDs and dispels the heat into the liquid via said heatsink faceplate keeping the UV-C LEDs at their normal operating temperature, and wherein said UV-C LEDs are mounted within said heatsink faceplate and powered by said battery and controlled by said power control board;
   f) a tactile switch mounted in said upper hemisphere;
   g) a power button mounted within said first end of said upper hemisphere; said power button sealing said first end and providing a user access to said tactile switch to control UV-C LEDs operational modes of the disinfection device; and
   wherein, during operation and while said disinfection device is floating in said liquid, said one or more UV-C LEDs emit microorganism killing UV-C light radiation downward and outward from said disinfection device into said liquid.

37. The disinfection device of claim 36, wherein said device is self-righting in liquid with said second end oriented downward and said first end oriented upwards.

38. The disinfection device of claim 36, wherein said power control board comprises a mounting substrate and electrical components and circuitry for operational control over the UV-C LEDs.

39. The disinfection device of claim 36, wherein said upper hemisphere and said lower hemisphere have clocking features for assisting the lining up of said hemispheres during manufacturing.

40. The disinfection device of claim 36, wherein said heatsink faceplate has a concave outward facing surface and wherein light from said UV-C LEDs emits outward and downward in an overlapping light emission pattern into said liquid during use.

41. The disinfection device of claim 36, wherein said disinfection device has a weight distribution that permits the device to automatically right itself in liquid with the second end oriented downward.

42. The disinfection device of claim 36, further comprising one or more of a waterproof micro USB, indicator LEDs, ferromagnetic plate, indicator LED light pipe and switch and indicator LED Power control board.

43. The disinfection device of claim 36, wherein said disinfection device has an outside diameter from $>0 \leq$ to about 2 inches for personal water bottle disinfection.

44. A method of disinfecting an amount of liquid that is held in a container comprising the steps of:
   a. initiating the disinfection device of claim 36 by depressing the power button to turn the UV-C LEDs on, and selecting the operational mode;

b. depositing the disinfection device in the container;
c. disinfecting the amount of liquid with ultra violet radiation from the UV-C LEDs.

* * * * *